US007198397B2

(12) United States Patent
Bennett et al.

(10) Patent No.: US 7,198,397 B2
(45) Date of Patent: Apr. 3, 2007

(54) LED ENDOSCOPE ILLUMINATOR AND METHODS OF MOUNTING WITHIN AN ENDOSCOPE

(75) Inventors: Hudson D. Bennett, New Braintree, MA (US); Robert J. Krupa, Leominster, MA (US); William F. LaFlash, Northbridge, MA (US); Matthew G. Maher, Worcester, MA (US); Thomas V. Root, Beverly, MA (US)

(73) Assignee: Optim, Inc., Sturbridge, MA (US)

( * ) Notice: Subject to any disclaimer, the term of this patent is extended or adjusted under 35 U.S.C. 154(b) by 0 days.

(21) Appl. No.: 11/229,321

(22) Filed: Sep. 16, 2005

(65) Prior Publication Data

US 2006/0085969 A1 Apr. 27, 2006

Related U.S. Application Data

(60) Provisional application No. 60/611,006, filed on Sep. 17, 2004.

(51) Int. Cl.
*A61B 1/06* (2006.01)

(52) U.S. Cl. .................................................. 362/574
(58) Field of Classification Search ................ 362/574, 362/800
See application file for complete search history.

(56) References Cited

U.S. PATENT DOCUMENTS

| 3,605,730 | A | * | 9/1971 | Hotchkiss .................... 362/198 |
| 4,385,344 | A | | 5/1983 | Gonser ........................ 362/32 |
| 4,639,845 | A | * | 1/1987 | Persson et al. ............. 363/132 |
| 5,634,711 | A | | 6/1997 | Kennedy et al. ............ 362/119 |
| 5,680,492 | A | | 10/1997 | Hopler et al. ................. 385/34 |
| 6,260,994 | B1 | | 7/2001 | Matsumoto et al. ........ 362/574 |
| 6,318,887 | B1 | | 11/2001 | Matsumoto ................. 362/574 |
| 6,331,156 | B1 | | 12/2001 | Haefele et al. ............. 600/179 |
| 6,438,302 | B1 | | 8/2002 | Utsui et al. ................. 385/117 |
| 6,692,431 | B2 | * | 2/2004 | Kazakevich ................ 362/574 |
| 6,730,731 | B2 | * | 5/2004 | Tobita et al. ............... 524/495 |
| 6,785,433 | B2 | * | 8/2004 | Tiefenthaler ................ 385/12 |

(Continued)

FOREIGN PATENT DOCUMENTS

DE 202 11713 11/2002

OTHER PUBLICATIONS

International Search Report for PCT Application No. PCT/US2005/033435 mailed on Jan. 27, 2006 (2 pgs).

*Primary Examiner*—Ali Alavi
*Assistant Examiner*—William J Carter
(74) *Attorney, Agent, or Firm*—Proskauer Rose LLP

(57) ABSTRACT

The present invention is directed to methods of mounting a light source, such as, for example a high-efficiency, high-power solid state light source (e.g., a LED) within a handle of an endoscope. One of the methods of the present invention includes removing a portion of a package surrounding the light source to expose a light source chip, positioning the exposed light source adjacent to a chassis within the handle and in contact with an end of a light guide bundle, translating the light source with the exposed light source chip about the end of the light guide while measuring light output from an illumination (i.e., distal) end of the light guide bundle with a photodetector, and securing the exposed light source to the chassis at a position in which maximum light output is measured.

21 Claims, 5 Drawing Sheets

U.S. PATENT DOCUMENTS

| | | |
|---|---|---|
| 6,832,849 B2 | 12/2004 | Yoneda et al. .............. 362/551 |
| 6,918,693 B2 | 7/2005 | Ota et al. ................... 362/574 |
| 6,921,920 B2 | 7/2005 | Kazakevich ................ 257/81 |
| 6,932,599 B1 | 8/2005 | Hartung ....................... 433/29 |
| 2002/0120181 A1 | 8/2002 | Irion .......................... 600/178 |
| 2003/0141507 A1 | 7/2003 | Krames et al. ............... 257/79 |
| 2003/0156430 A1 | 8/2003 | Ota et al. ................... 362/574 |
| 2003/0231843 A1 | 12/2003 | Colombo et al. ........... 385/115 |
| 2003/0235800 A1 | 12/2003 | Qadar ......................... 433/29 |
| 2004/0004846 A1 | 1/2004 | Steen et al. ................. 362/555 |
| 2004/0049172 A1 | 3/2004 | Root et al. ..................... 606/1 |
| 2004/0246744 A1 | 12/2004 | Krupa et al. ............... 362/574 |

* cited by examiner

LED ENDOSCOPE ILLUMINATOR AND METHODS OF MOUNTING WITHIN AN ENDOSCOPE

CROSS REFERENCE TO RELATED APPLICATION

This application claims the benefit of the filing date of U.S. Provisional Patent Application Ser. No. 60/611,006, filed on Sep. 17, 2004, the entirety of which is incorporated herein by reference.

FIELD OF THE INVENTION

This invention relates to a remote illumination device using a high-power LED and a fiber optic light guide.

BACKGROUND OF THE INVENTION

Light sources for endoscopic use are generally of two types: incandescent filament lamps and arc lamps. Incandescent lamps produce light by passing current through a tungsten filament, causing it to radiate light in proportion to its blackbody color temperature. The hotter the filament, the higher its color temperature and the more nearly it approaches daylight with a color temperature of approximately 5500K. Tungsten filament lamps range in color temperature from approximately 2400–3400K. Because of the low color temperature, objects illuminated by a tungsten filament light source appear slightly yellow due to the low output of blue light from these sources. Arc lamps produce light by creating a plasma between two electrodes within the sealed bulb. White light from these lamps can be produced by choosing the appropriate fill gas (usually Xe) and pressure (usually several atmospheres). Color temperature of common arc lamps is approximately 4000–6000K. Both types of lamps, filament and arc, are very inefficient in converting electrical power to light, and consequently produce large amounts of heat. The heat must be dissipated. It also contributes to a shortened useful life of such light sources.

There have been numerous attempts to utilize low power (<1 W electrical power consumption, typically operating below 100 mW) LEDs coupled to fiber optic light guides as light sources for endoscopy, dentistry, and for remote illumination of objects (as with a flashlight). Most of these prior attempts employ numerous low power LEDs for remote illumination. Multiple LEDs are necessary because the light output from a single, low power LED is very low and there is poor coupling of light emitted by the LED(s) into the optical fiber. An example of several coupling methods appears in U.S. Pat. No. 6,331,156 whereby the inventors place the fiber optic directly in front of either a surface mount or cylindrical LED without the use of additional optical components, coatings or gel. This patent also exemplifies the use of additional optical components in the form of lenses or mirrors in order to collect light generated from a standard, unmodified LED package configuration. US published patent application 2004/0004846 A1 utilizes a lens to couple the light emitted by an LED into a fiber optic. US published patent application 2003/0156430 A1 describes a device that consists of a number of individual LEDs mounted on mirrors, the arrangement of the LEDs and mirrors having a common focal point at the input end of the fiber light guide. U.S. Pat. No. 6,260,994 describes a plurality of LEDs mounted between a spherical or parabolic reflector and a lens, which directs the light emitted by the LEDs into the light guide fiber. In this invention, the LEDs emit light towards the collecting lens and away from the reflector. In U.S. Pat. No. 6,318,887, the LEDs are positioned so as to emit radiation towards a reflector, which then reflects light through a transparent printed circuit board and towards a lens and fiber light guide. In US published patent application 2002/0120181 A1, light emitted by several LEDs is collected along a common optical axis through a series of beam splitting prisms, in at least one embodiment with the use of lenses to couple the light from the LED into the prism, and then into the fiber. In these examples, the LED packages are not modified; multiple, low power LEDs are employed in order to attain a reasonable level of illumination; and in most of these examples, external optical components are employed in order to increase the coupling efficiency between the LEDs and the light guide fiber.

In US published patent application 2003/0231843, numerous low power LEDs are coupled into individual fibers, which are combined together at the distal end of the device to produce intense light for curing dental epoxy. This patent application describes an approach in which the LED package and light guide fiber are modified in order to increase the optical coupling efficiency between the two. In one embodiment, the cladding material from the fiber is removed and the fiber core is placed within the LED epoxy lens. The exterior of the epoxy lens is coated with a low refractive index "clad" that produces total internal reflection of the light emitted by the LED. Some of the light reflected by this LED clad can make its way into the core of the fiber and be transmitted to the distal end of the device. This patent application also includes a description of a taper attached to the external surface of the LED dome lens that couples the light into the fiber. Again, however, additional optical elements (cladding or tapers applied to the LED) are used. Also, the device employs numerous low power LEDs to attain sufficient light output from the device. This type of arrangement would be difficult if not impossible to implement with a high power LED because of the high operating temperature of these LEDs (up to 135 degrees C). At high temperatures, the epoxy used in typical LED packages will melt or crack due to thermal cycling. In addition, high temperatures will cause the epoxy to discolor, typically becoming yellow. This will impart a yellow cast to the light, thereby lowering its effective color temperature and its desirability as a visual light source. In addition, discoloration will absorb lower wavelengths of light emitted by the LED, particularly those wavelengths in the blue and UV region of the spectrum that are essential for epoxy curing and fluorescence applications.

SUMMARY OF THE INVENTION

Recent advances in light emitting diodes (LEDs) have seen the advent of very high power LEDs, up to 5 W. This invention utilizes a high power white light LED as a light source for medical and industrial endoscopes. The high power, very small size, and high efficiency of these devices makes it possible to design an untethered endoscope; an endoscope without a light guide umbilical connecting the endoscope to an external light source. As a result, in some embodiments, the invention is directed to an endoscope with a light source mounted within a handle of the endoscope. In certain embodiments, a battery to power the light source is also positioned in the handle so that the endoscope is untethered. An advantage of this embodiment is that a user has full range of motion without being tied to an external power source. In addition, another advantage is that the endoscope is light in weight.

In general, the invention relates to an endoscope with a battery powered, high power LED incorporated into the endoscope handle. By close coupling of a light guide bundle to the LED without the use of additional optical components, a large amount of the light emitted by the LED can be coupled directly into the fibers of the light guide bundle. As a result, a greater amount of light from the LED can be transmitted to the distal end of the endoscope which illuminates objects under investigation. Embodiments of the present invention do not include auxiliary optics, such as lenses or mirrors, disposed between the light source and the light guide bundle, but instead rely on the small size of the LED's emitting region and the close placement (e.g., direct contact or close proximity) of the light guide bundle to the emitting region. Because the LED itself is very efficient in converting electrical energy into light and the described optical interface is very efficient at coupling this light from the LED into the light guide fiber, this new light source can be powered by small batteries that will operate for a considerable length of time without the need for battery replacement or recharging, and without making the endoscope handle cumbersome or unwieldy. The lack of auxiliary optics between the light source and the light guide bundle simplifies the mechanical design and volume of space within the handle needed for the light source. The high light output and high coupling efficiency of the light emitted by the LED into the light guide fiber increases battery lifetime and/or permits the use of smaller capacity, and smaller volume batteries.

In one aspect, the invention is directed to a method of mounting a light source within a handle of an endoscope. The method includes the following steps: removing a portion of a lens and an index matching solution from a light source package to expose a portion of a light source chip and form an exposed light source package; positioning the exposed light source package so that a securing surface of the exposed light source package is disposed adjacent to a chassis within the handle of the endoscope and a light emitting surface of the exposed light source package is in contact with a contact end of a light guide bundle, the light guide bundle extending from the contact end to an illumination end disposed on the working end of the endoscope; translating the exposed light source package about a plane containing the contact end while measuring light output from the illumination end with a photodetector to align the exposed light source package with the contact end; and securing the exposed light source package to the chassis at the position in which maximum light output is measured.

This aspect of the invention can include one or more of the following features. In some embodiments, the light mounted is a LED. In certain embodiments, the chassis is formed of a metal (e.g., aluminum) and a layer of thermally conductive grease is disposed between the securing surface and the chassis to facilitate conduction of heat from the exposed light source package. In some embodiments, the exposed light source package is secured to the chassis with screws, such as for example screws that are formed of a non-conductive material. In certain embodiments, the exposed light source package is battery powered, and may be conditioned to provide constant power to the light source chip, such as for example by a pulse width modulation circuit.

In another aspect, the invention is directed to a method of mounting a LED within a handle of an endoscope. The method includes the following steps: positioning a LED including a LED chip supported by a securing surface and having an exposed light emitting surface so that the securing surface is disposed adjacent to a chassis within the handle of the endoscope and the light emitting surface is in contact with a contact end of a light guide bundle, the light guide bundle extending from the contact end to an illumination end disposed on the working end of the endoscope; translating the exposed LED package about a plane containing the contact end while measuring light output from the illumination end with a photodetector to align the exposed LED package with the contact end; and securing the exposed LED package to the chassis at the position in which maximum light output is measured.

This aspect of the invention can include one or more of the following features. In some embodiments, the chassis is formed of a metal (e.g., aluminum) and a layer of thermally conductive grease is disposed between the securing surface and the chassis to facilitate conduction of heat from the exposed LED package. In certain embodiments, the LED is secured to the chassis with screws, such as for example that are formed of a non-conductive material. In some embodiments, the LED package is battery powered, and may be conditioned to provide constant power to the LED chip. In certain embodiments, the battery powered exposed LED package is conditioned by a pulse width modulation circuit.

While the above embodiments have been described as relating to endoscopes (e.g., medical endoscopes, industrial endoscopes), this invention also has applications in other areas, such as, for example, fiber optic lighting for microscopy, fiber optic lighting for still and video photograph. In addition, this invention can also be applied to other regions of the light spectrum, such as ultraviolet, near infrared, and infrared and can be used in other types of optical observations, such as florescence, absorbance, and transmittance measurements.

BRIEF DESCRIPTION OF THE DRAWINGS

Other objects, features and advantages will occur to those skilled in the art from the following description of the preferred embodiments, and the accompanying drawings, in which.

DETAILED DESCRIPTION OF THE PREFERRED EMBODIMENTS

Figure 1:
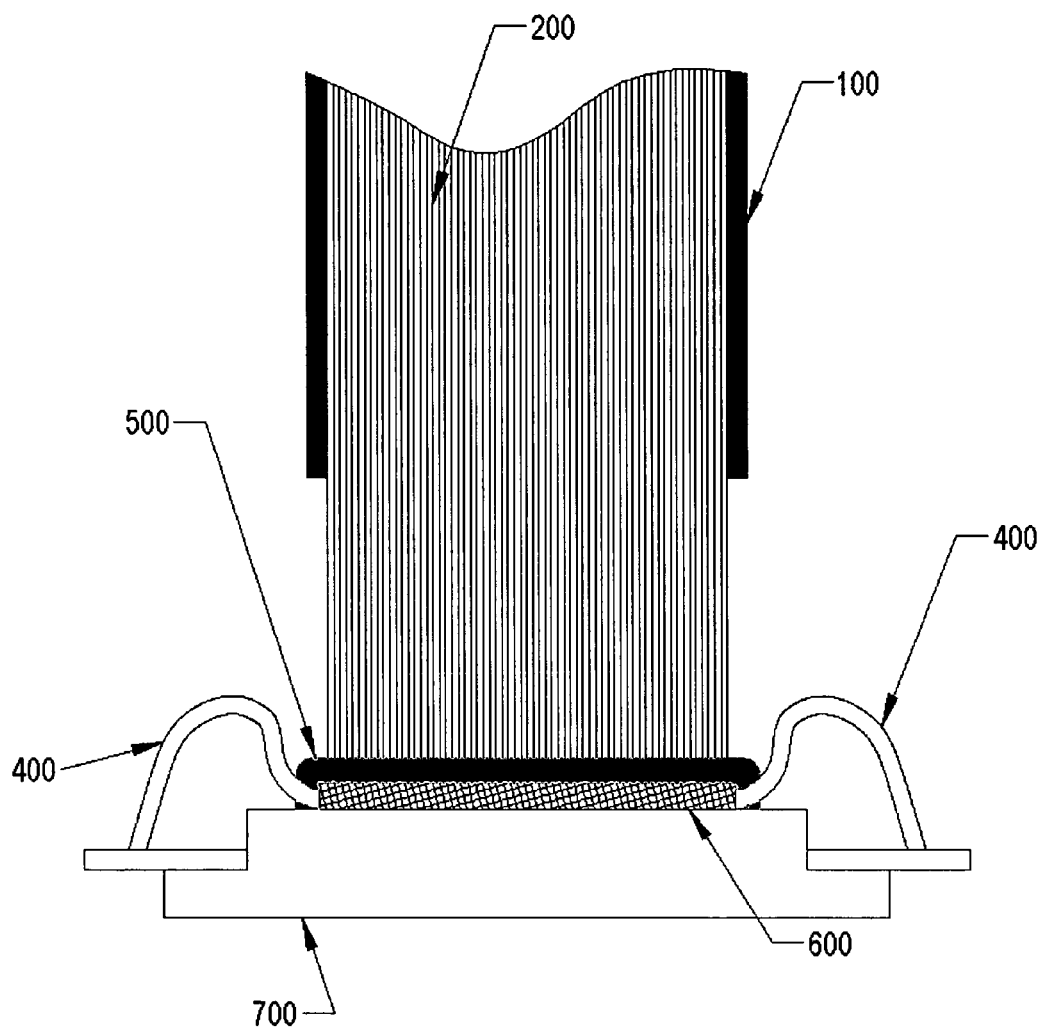
FIG. 1 is an enlarged partial cross sectional diagram of one embodiment of the high power LED-based light source of the invention.

One embodiment of this invention utilizes a high power LED (Luxeon III Model LXHL-LW3C, Lumileds Lighting, LLC, 370 W, Trimble Road, San Jose, Calif. 95131) with a typical forward voltage of 3.7V and operating current at 700 mA. This device can be safely operated up to a current of 1 A with a corresponding typical forward voltage of 3.9V. This white LED has a typical color temperature of 5500K. The LED chip has an emitting surface of approximately 1 mm=1 mm, and is coated with a wavelength conversion phosphor (and/or fluorophor) that emits a broadband continuum of visible white light between about 470–700 nm.

The light emitting area of the LED is coupled to a small 1 mm square or round bundle of light guide fibers; a typical light guide bundle size used in endoscopes. The light guide bundle is composed of hundreds of individual glass (or plastic) fibers grouped together to form a single bundle at the light source, and either a single bundle or multiple bundles at the distal end of the endoscope. Such bundles can take on a variety of shapes at the distal end depending upon the design of the particular endoscope: one or more round bundles, a circular halo, a crescent, or the like. Small diameter fibers, typically 30–50 micrometers in diameter, are employed because these small fibers are flexible (necessary for flexible endoscopes that bend during use), or because they are required to fit into the narrow spaces around the optics either in the shaft or distal head of the endoscope.

Other types of light guides can be coupled to the LED in the manners described herein, including: liquid light guides, plastic or glass fibers, plastic or glass rods, and tapers made from fibers (glass and plastic) or solid tapers (glass and plastic). Single glass or plastic fibers may comprise the light guide. Such fibers around 1 mm in diameter are typically flexible. In order to accommodate a small light guide bundle of less than the LED emitting area, a fiber optic or solid plastic or glass taper may be placed between the LED emitting surface and the bundle, acting as an adapter that captures substantially all of the light emitted from the LED and efficiently couples it into the fiber bundle that delivers the light to the distal end of the instrument.

The details of the endoscope or other device in which the light source is used are known to those skilled in the art, for example as disclosed in U.S. Pat. No. 6,260,994 (incorporated herein by reference in its entirety). This holds true whether the light source is used in a medical or industrial endoscope (either flexible or rigid) or other application areas such as fiber optic lighting, delivery of light from other regions of the spectrum, other types of optical observations such as fluorescence, absorbance, and transmittance measurements, and remote light sources akin to fiber optic flashlights, used primarily for visual inspection.

The high-power white light-emitting LED chip is commercially supplied encapsulated in a silicone optical gel covered by a plastic dome lens assembly, which spreads the emitted light over a 160 degree angle (total included angle at which 90% of the total luminous flux is captured). A considerable amount of light can be captured by placing the light guide at the surface of this dome lens or utilizing additional optical components (lenses, mirrors, tapers, etc.) to couple the light into the fiber bundle. However, a much larger portion of light can be captured by moving the light guide adjacent to the surface of the LED chip.

FIG. 1 demonstrates how the maximum coupling of light from the LED chip into the light guide is achieved. The plastic lens and coupling gel as supplied with the LED are first removed, exposing the LED chip 600 and its phosphor coating 500. LED chip 600 is supplied mounted on heat sink 700. Wires 400 supply power to LED chip 600. A bundle of polished light guide fibers 200 having a flat face (typically filling the entire emitting area of chip 600) is epoxied into a stainless steel ferrule 100, which is ideally the same shape and size as the LED chip emitting surface area. Other materials can be used for the construction of the ferrule, such as other metals, alloys, and plastics, or the ferrule can be eliminated altogether when not needed for grouping a large number of fibers together (such as when a single, large diameter fiber or rod is used instead of a group of fibers). The end of ferrule 100 can be coincident with the light guide 200 face, or can be slightly recessed from the face of the polished light guide 200 in order to reduce the size of the end of this light guide. The polished light guide 200 face is placed in contact with the surface of LED chip 600, or as close to this surface as mechanically possible. Ideally, both faces are as flat as possible, which accomplishes actual contact or very minute separation across all or a substantial portion of the interface between the LED surface and the face of the light guide. The flexibility of the light guide fibers can assist in a higher degree of contact between the two faces. This ensures the most efficient coupling of light out of LED chip 600 into light guide 200.

Figure 2:
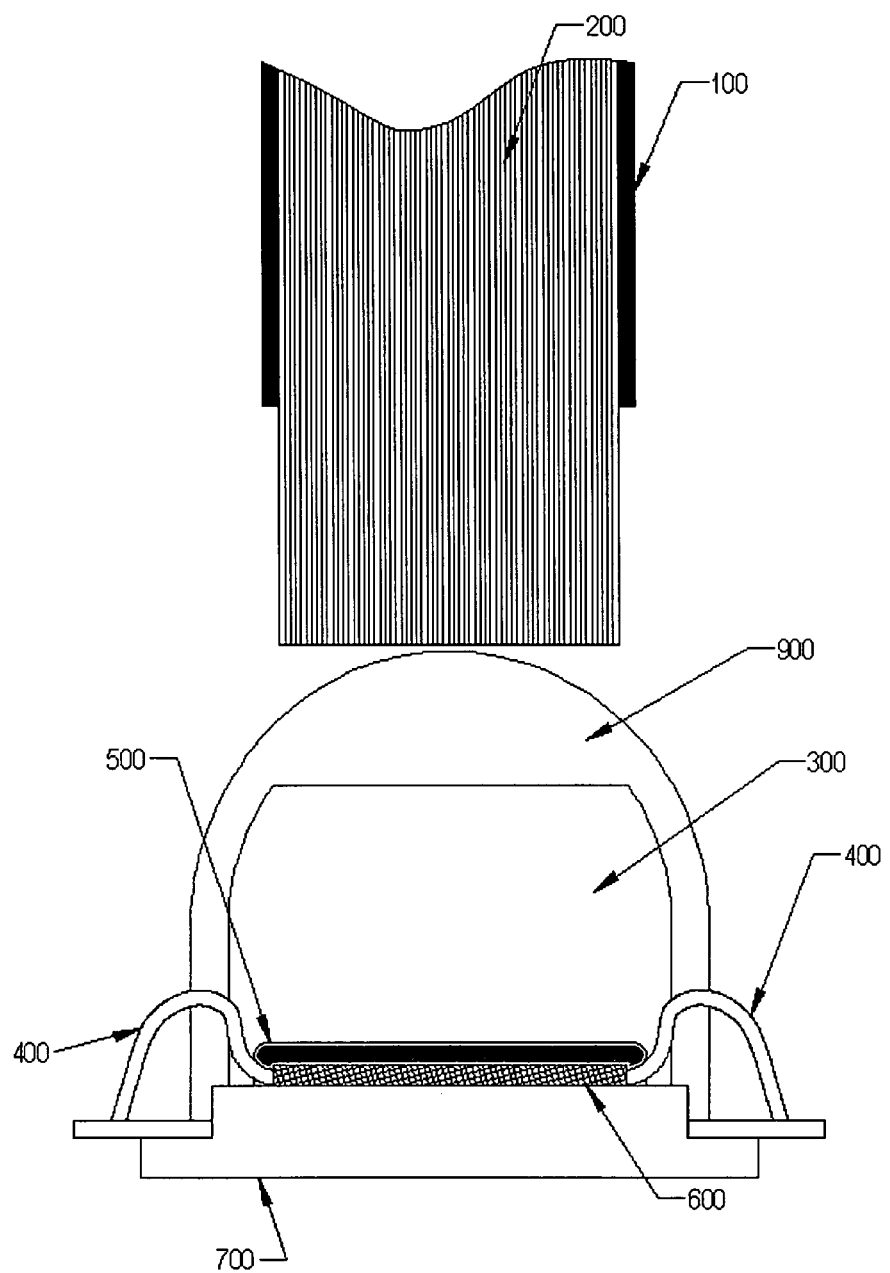
FIG. 2 is a similar diagram for an alternative embodiment of the inventive light source.
Figure 3:
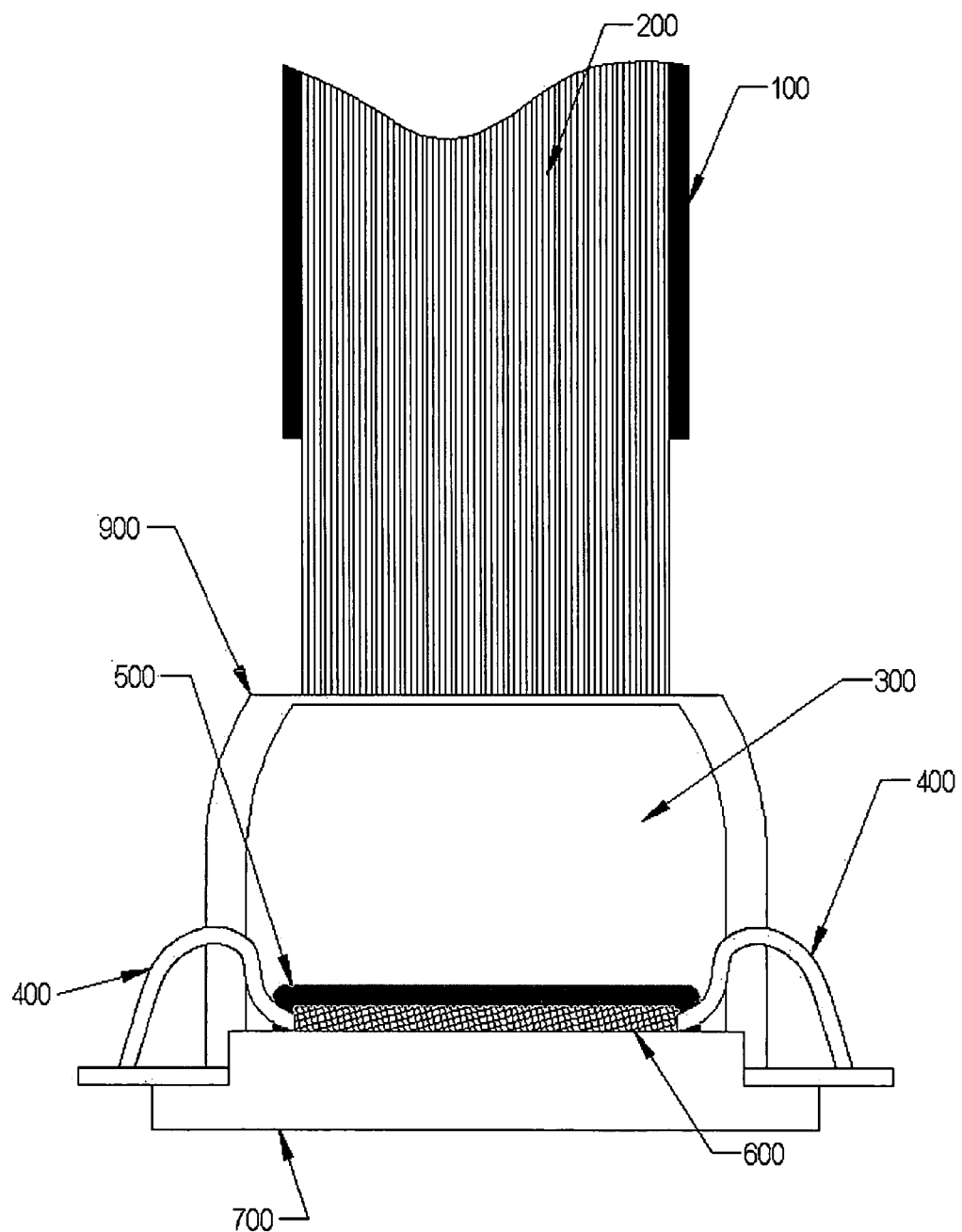
FIG. 3 is a similar diagram of yet another alternative embodiment of the light source of this invention.

Other embodiments of the invention are also anticipated and are now described. FIGS. 2 and 3 demonstrate how the LED can be coupled to a light guide with little or no modification to the LED housing. In FIG. 2, light guide 200 is placed directly adjacent to the LED dome lens 900. Sufficient light may be coupled into light guide 200 to illuminate the object of interest. However, the optical transfer efficiency of this coupling is very poor, resulting in a lower level of illumination of the object as compared to the preferred embodiment described above. This can be compensated at least in part by operating at higher power, which may increase the light output but also lowers battery and LED lifetime.

In FIG. 3, dome lens 900 of the LED is ground and polished nearly down to the level of internal silicone encapsulent 300, so as to preserve the integrity of the mechanical package. This increases the amount of light available to light guide 200, as the amount of light present at any plane above the surface of LED chip 600 is inversely proportional to the distance between this plane and the LED chip. Therefore, if the distance from the LED chip to the light guide's polished face is reduced from 3 mm to 2 mm, an increase in light density (light per unit area) of 2.25 times is achieved. To further improve the amount of light coupled into light guide 200, an index matching material (not shown) can be placed between the LED's dome lens 900 and light guide 200.

Figure 4:
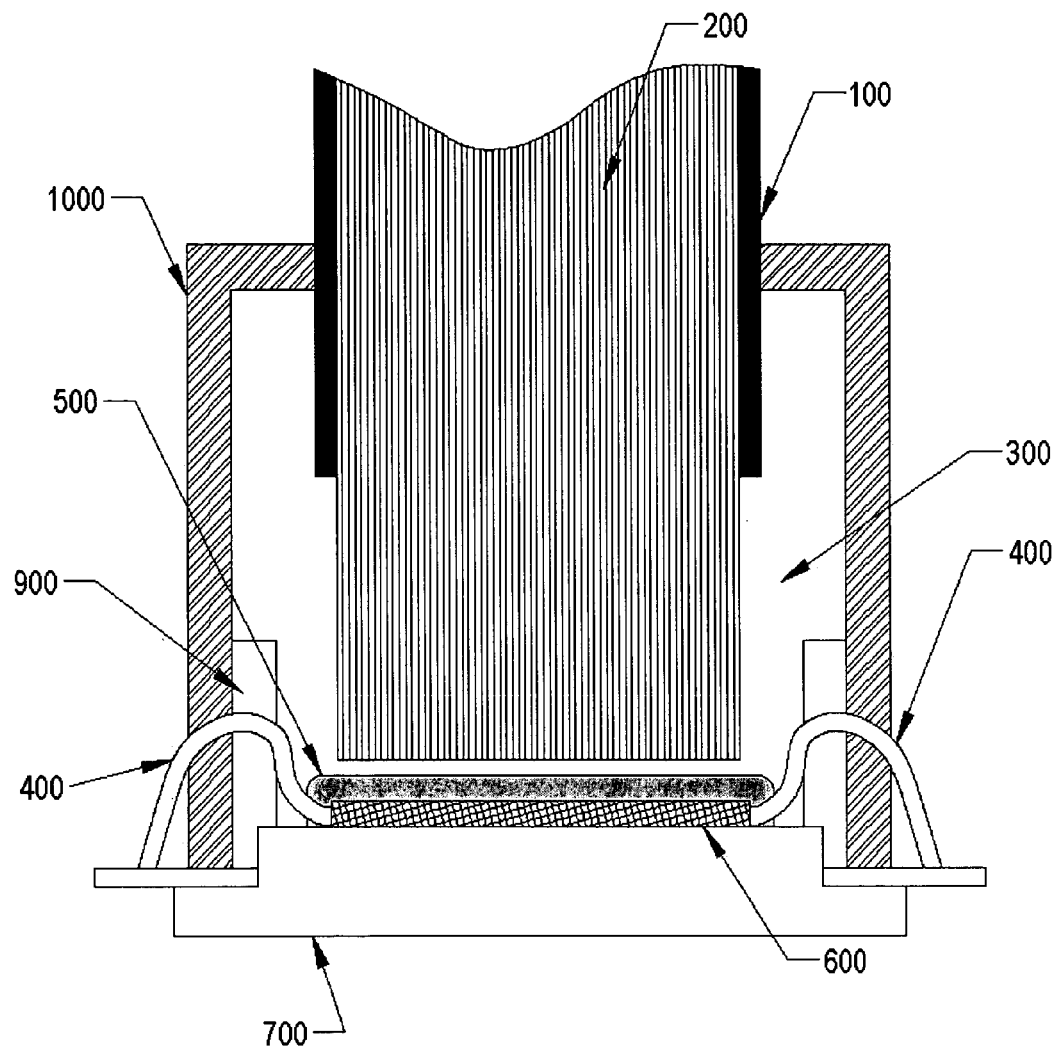
FIG. 4 is a alternative view of another embodiment of the inventive light source.

FIG. 4 depicts yet another embodiment of the invention in which LED dome lens 900 is partially removed so as to expose the LED's silicone encapsulent material 300 that encapsulates LED chip 600 and phosphor 500. Light guide 200 can then be immersed in the LED's index matching material 300, and placed in close proximity to the emitting surface of the LED. This can be accomplished without the need to disturb the original index matching material 300, thereby avoiding the possibility of introducing air bubbles within the optical path. Care should be taken so as not to introduce air between light guide 200 and silicone encapsulent 300. This can be accomplished by assembling the components in a vacuum glove box, or by inclining light guide 200 at a slight angle when placing it in silicone encapsulent material 300. As light guide 200 is lowered into silicone encapsulent 300, the fiber is slowly inclined back towards perpendicularity with respect to LED chip 600 without trapping air bubbles at the interface. Sleeve 1000 can then be inserted over ferrule 100 and the LED assembly, and fastened in place either with adhesives or by mechanical means. This will hold light guide 200 in place and prevent silicone encapsulent 300 from flowing out of modified dome lens 900 at a later time. Sleeve 1000 is optional.

In some instances, it is desirable to employ an index matching material between the fiber bundle and the LED chip, or the combination of the LED chip and its phosphor. The index matching material helps to couple the emitted light into the light guide, and typically has an index of refraction between that of the light emitting surface and that of the light guide. The material can be a gel. Examples of when an index matching material is desirable are: when the emitting surface is a substrate that the LED chip is mounted to, such as sapphire (n=1.76, where "n" is the refractive index), or when the LED chip is the emitting surface and it possesses a high refractive index. Examples of LED chips with very high refractive indices include chips manufactured from gallium nitride (n=2.5), gallium phosphide (n=3.31), and gallium arsenide (n=4.02). The amount of light coupled into the light guide from the LED can be increased, potentially by up to a factor of two, when an appropriate index matching material is employed between the LED and the fiber. The index matching material may also substitute for the silicone encapsulent 300; the silicone encapsulent 300 being a specific type of index matching material.

While the preferred embodiment of this invention utilizes a Luxeon III LED with a 1 mm square emitting surface, other LED package designs also lend themselves to the inventive technique of capturing light by a light guide, which may be accomplished with a fiber bundle. Some examples of these other package designs include the industry standard T1 (3 mm) and T1-¾ (5 mm) packages in which the LED chip is enclosed in an epoxy dome lens. It is readily apparent to those skilled in the art to understand how the epoxy package can be removed down to the level of the LED chip and coupled to the light guide. Similarly, the flat package design of the Microsemi (Microsemi Corporation, 580 Pleasant Street, Watertown, Ma. 02472) UPW3LEDxx readily lends itself to fiber coupling by directly bonding the light guide fiber to the face of the window adjacent to the LED chip, with or without an index matching material between the window and the fiber as is described in FIG. 4, substituting an index matching gel for the silicone encapsulent.

Figure 5:
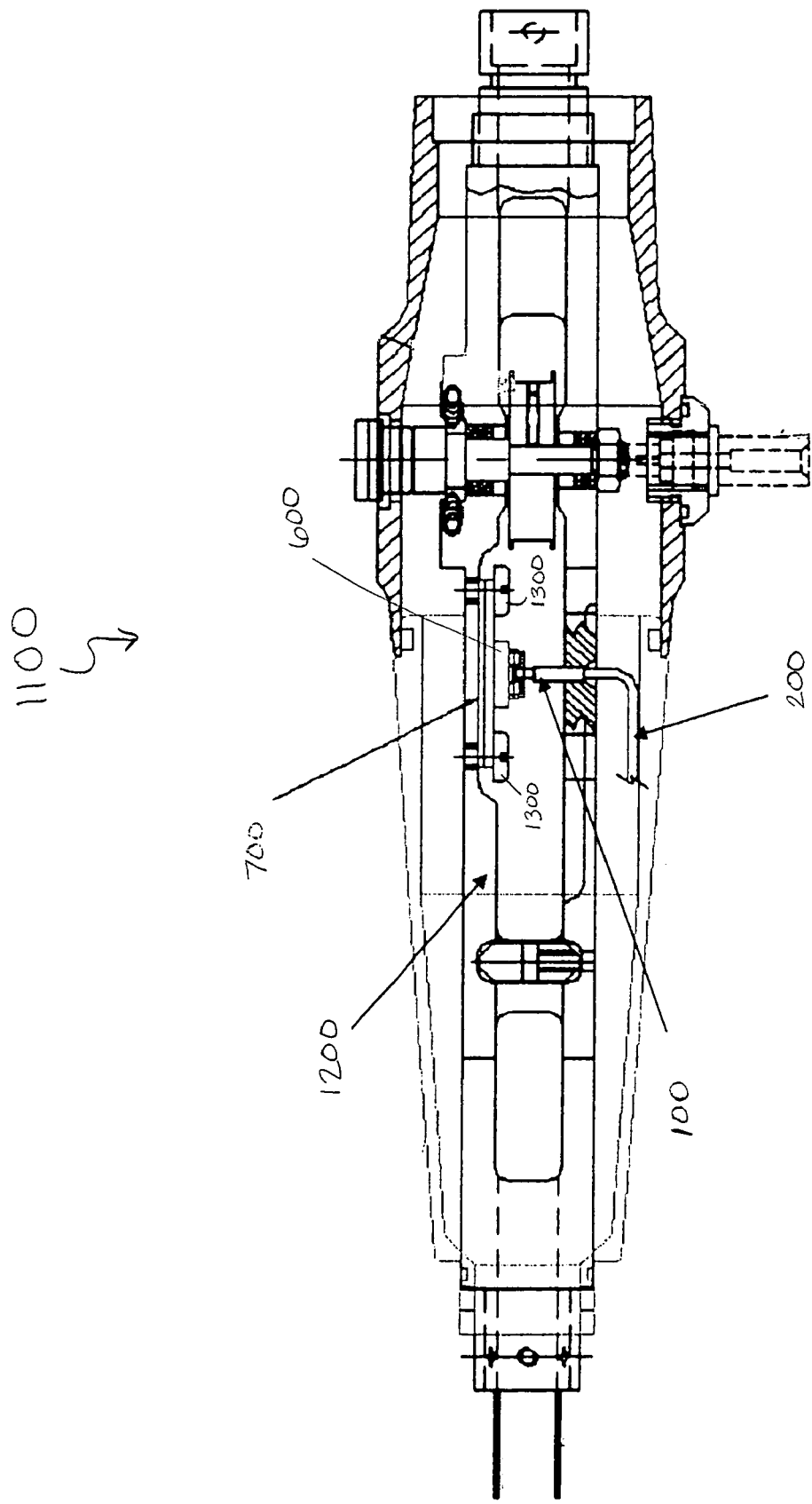
FIG. 5 depicts the mounting of the LED in the handle of a nasopharyngoscope.

FIG. 5 depicts the mounting of the light source (e.g., LED) in a handle 1100 of a nasopharyngoscope. After removing the packing to expose the LED chip 600 as described above, the LED is attached to an aluminum endoscope chassis 1200 and handle via two nylon screws 1300. The interface of the LED to the aluminum chassis is coated with a thin layer of thermally conductive grease to facilitate conduction of the heat from the LED's heat sink 700 into the endoscope chassis 1200 and handle 1100 where it is dissipated by convection. The light guide ferrule 100 is aligned with the LED's emitting surface by moving the LED in the X-Y plane before it is secured to the chassis 1200 by the screws 1300. A photodiode measures the output of the light guide cable 200 during this process. Once a maximum is reached in the light guide's output, the screws 1300 are tightened, securing the LED in place. The light guide 200 is then lowered until it comes into contact with the surface of the LED's emitting surface, and secured to the chassis by epoxy.

Power for the LED is supplied by a rechargeable lithium ion battery. The battery is connected to the endoscope handle via a DC connector mounted in the handle, occupying the traditional position of a light guide umbilical cable or light guide post. Two multistrand wires connect the LED to the battery connector. Power from the battery is unregulated in one embodiment, but can be conditioned by a pulse width modulation circuit in other embodiments to provide a more constant power to the LED. Because the nominal operating voltage of the LED is 3.6V and the lithium ion battery, fully charged, is nominally 3.6–3.9V the LED operates initially at full power (about 800 mA of current) and slowly decreases in power as the battery's voltage and current drop. With a 1650 mA-hour lithium ion battery, this provides approximately 2 hours of useful light output for the endoscope before the battery requires recharging.

Other embodiments will occur to those skilled in the art and are within the following claims.

What is claimed is:

1. A method of mounting a light source within a handle of an endoscope, the method comprising:
   removing a portion of a lens and an index matching solution from a light source package to expose a portion of a light source chip and form an exposed light source package;
   positioning the exposed light source package so that a securing surface of the exposed light source package is disposed adjacent to a chassis within the handle of the endoscope and a light emitting surface of the exposed light source package is in contact with a contact end of a light guide bundle, the light guide bundle extending from the contact end to an illumination end disposed on the working end of the endoscope; and
   securing the exposed light source package to the chassis at the position in which maximum light output is measured.

2. The method of claim 1, wherein the light source is a LED.

3. The method of claim 1 wherein the chassis is formed of a metal and a layer of thermally conductive grease is disposed between the securing surface and the chassis to facilitate conduction of heat from the exposed light source package.

4. The method of claim 3 wherein the chassis is formed of aluminum.

5. The method of claim 1 wherein the exposed light source package is secured to the chassis with screws.

6. The method of claim 5 wherein the screws are formed of a non-conductive material.

7. The method of claim 1 wherein the exposed light source package is battery powered.

8. The method of claim 7 wherein the battery powered light source package is conditioned to provide constant power to the light source chip.

9. The method of claim 8 wherein the battery powered light source package is conditioned by a pulse width modulation circuit.

10. The method of claim 1, further comprising prior to securing the exposed light source package to the chassis, translating the exposed light source package about a plane containing the contact end while measuring light output from the illumination end with a photodetector to align the exposed light source package with the contact end.

11. The method of claim 1, wherein the chassis is formed of a metal and a layer of thermally conductive epoxy is disposed between the securing surface and the chassis to facilitate conduction of heat from the exposed light source package.

12. A method of mounting a LED within a handle of an endoscope, the method comprising:
   positioning a LED including a LED chip supported by a securing surface and having an exposed light emitting surface so that the securing surface is disposed adjacent to a chassis within the handle of the endoscope and the light emitting surface is in contact with a contact end of a light guide bundle, the light guide bundle extending from the contact end to an illumination end disposed on the working end of the endoscope; and
   securing the exposed LED package to the chassis at the position in which maximum light output is measured.

13. The method of claim 12 wherein the chassis is formed of a metal and a layer of thermally conductive grease is disposed between the securing surface and the chassis to facilitate conduction of heat from the exposed LED package.

14. The method of claim 12 wherein the chassis is formed of aluminum.

15. The method of claim 12 wherein the LED is secured to the chassis with screws.

16. The method of claim 15 wherein the screws are formed of a non-conductive material.

17. The method of claim 12 wherein the exposed LED package is battery powered.

18. The method of claim 17 wherein the battery powered exposed LED package is conditioned to provide constant power to the LED chip.

19. The method of claim 18 wherein the battery powered exposed LED package is conditioned by a pulse width modulation circuit.

20. The method of claim 12, wherein the chassis is formed of a metal and a layer of thermally conductive epoxy is disposed between the securing surface and the chassis to facilitate conduction of heat from the exposed LED package.

21. The method of claim 12, further comprising prior to securing the exposed LED package to the chassis, translating the exposed LED package about a plane containing the contact end while measuring light output from the illumination end with a photodetector to align the exposed LED package with the contact end.

* * * * *